(12) United States Patent
Sater et al.

(10) Patent No.: US 8,016,857 B2
(45) Date of Patent: Sep. 13, 2011

(54) VASCULAR PUNCTURE CLOSURE

(75) Inventors: Ghaleb Sater, Acton, MA (US); Matthew Spurchise, Peabody, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 677 days.

(21) Appl. No.: 12/105,448

(22) Filed: Apr. 18, 2008

(65) Prior Publication Data

US 2009/0264919 A1    Oct. 22, 2009

(51) Int. Cl.
*A61B 17/08* (2006.01)
(52) U.S. Cl. .......................................... 606/213
(58) Field of Classification Search .................. 606/139, 606/144, 148, 151, 213, 198, 200, 214–215; 600/37; 623/1.11, 23.72–23.74
See application file for complete search history.

(56) References Cited

U.S. PATENT DOCUMENTS

| | | | |
|---|---|---|---|
| 4,655,219 A * | 4/1987 | Petruzzi | 606/206 |
| 4,702,250 A * | 10/1987 | Ovil et al. | 606/148 |
| 5,397,331 A | 3/1995 | Himpens et al. | |
| 5,405,360 A * | 4/1995 | Tovey | 606/151 |
| 6,287,323 B1 | 9/2001 | Hammerslag | |
| 6,391,048 B1 | 5/2002 | Ginn et al. | |
| 6,428,546 B1 * | 8/2002 | Cancel et al. | 606/108 |
| 6,767,356 B2 | 7/2004 | Kanner et al. | |
| 6,890,342 B2 * | 5/2005 | Zhu et al. | 606/213 |
| 7,500,946 B2 * | 3/2009 | Lau et al. | 600/37 |
| 7,727,142 B2 * | 6/2010 | Hjelle et al. | 600/37 |
| 7,736,299 B2 * | 6/2010 | Klenk et al. | 600/37 |
| 2003/0100920 A1 * | 5/2003 | Akin et al. | 606/213 |
| 2005/0149115 A1 * | 7/2005 | Roue et al. | 606/213 |
| 2005/0182290 A1 * | 8/2005 | Lau et al. | 600/37 |
| 2006/0106420 A1 * | 5/2006 | Dolan et al. | 606/213 |
| 2007/0049968 A1 * | 3/2007 | Sibbitt et al. | 606/213 |
| 2007/0191884 A1 * | 8/2007 | Eskridge et al. | 606/213 |
| 2009/0216264 A1 * | 8/2009 | Friedman et al. | 606/213 |

* cited by examiner

*Primary Examiner* — Darwin P Erezo
*Assistant Examiner* — Son Dang

(57) ABSTRACT

An apparatus for placing a patch over a puncture wound in a blood vessel exteriorly of the vessel includes a device for delivering the patch in a folded form and then expanding the patch from its unfolded configuration while deploying the patch about the region of the vessel puncture.

7 Claims, 7 Drawing Sheets

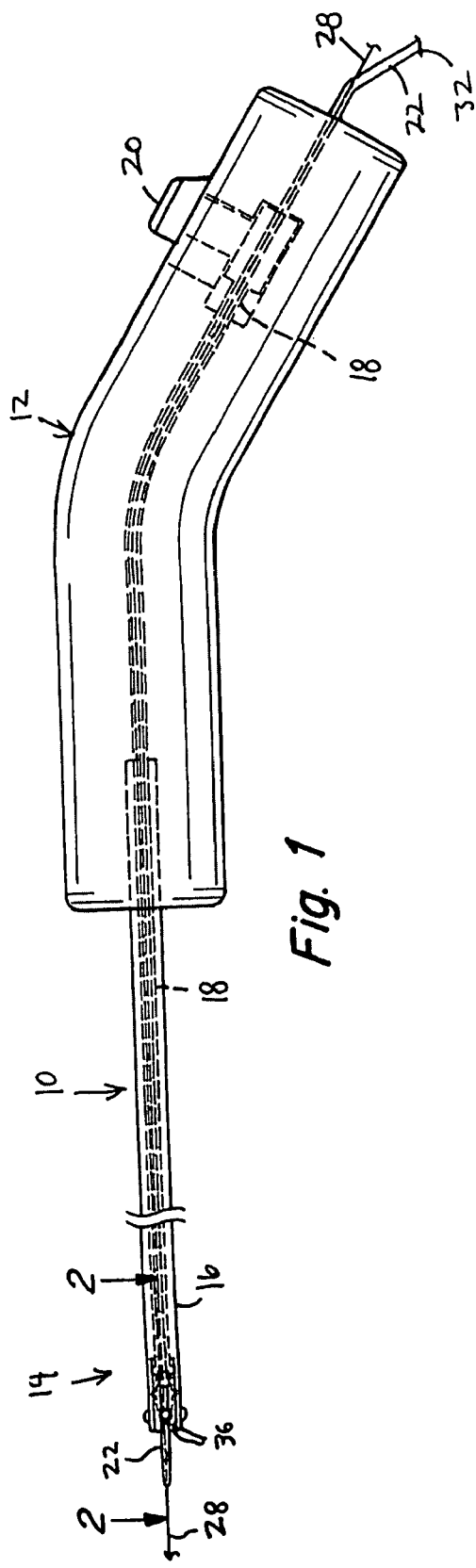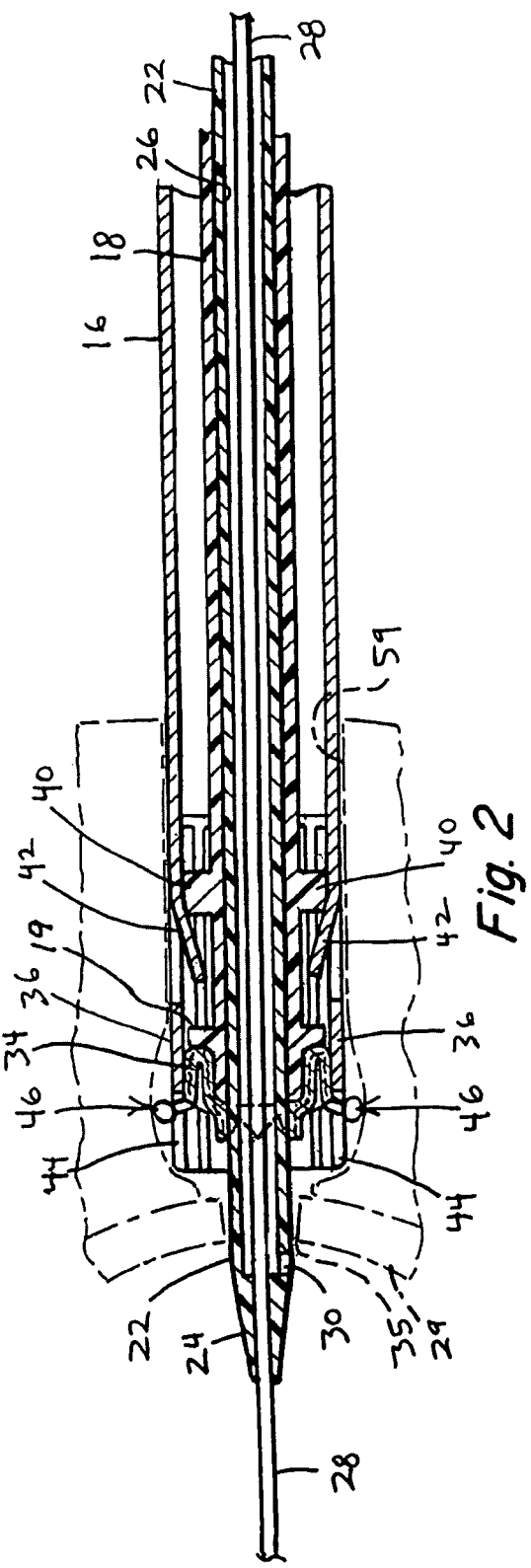

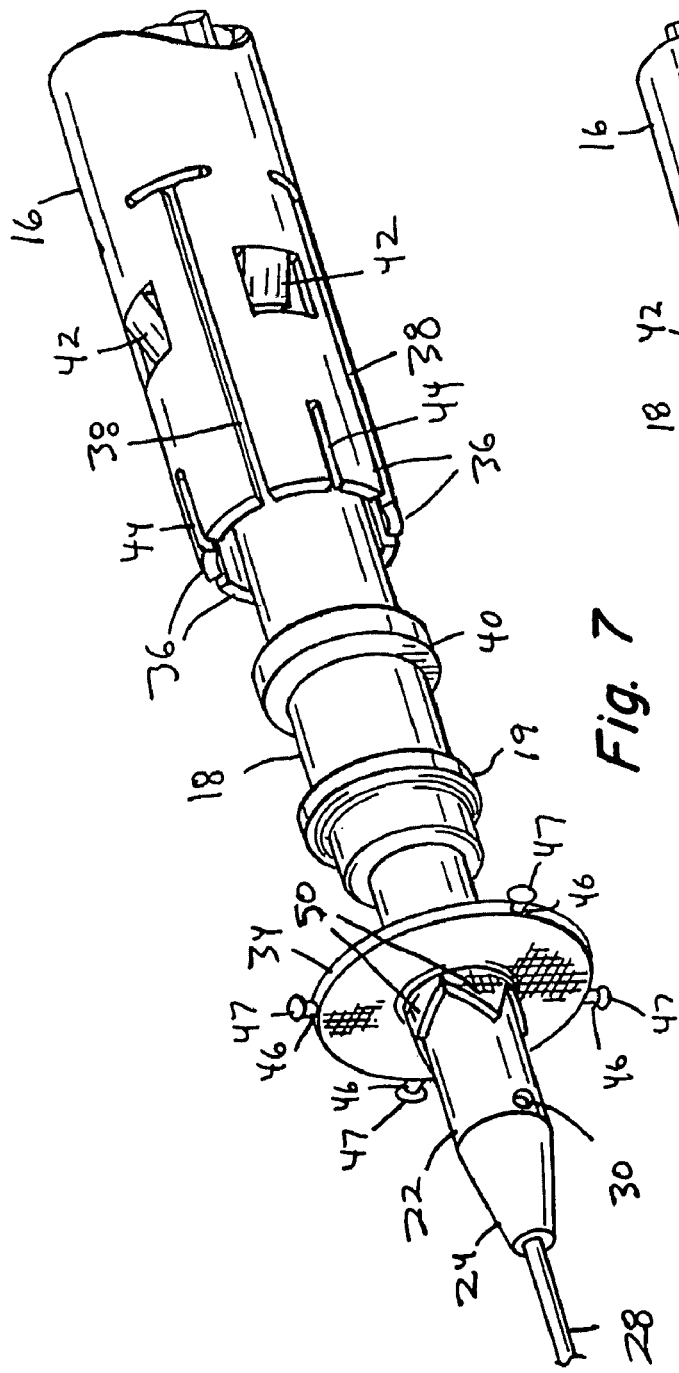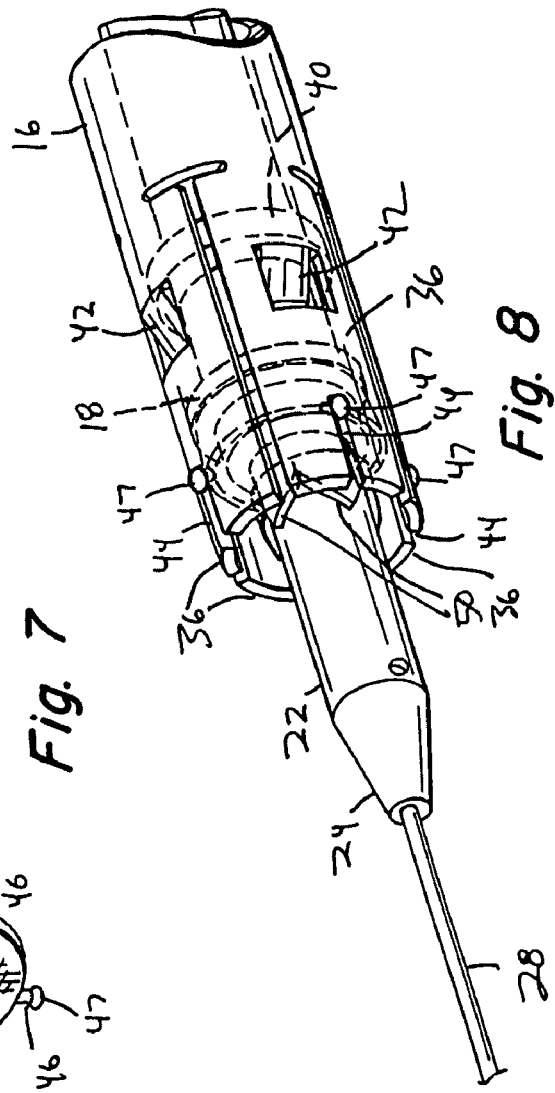

VASCULAR PUNCTURE CLOSURE

FIELD OF THE INVENTION

The invention relates to devices and techniques for closing a puncture in a blood vessel after an intravascular procedure and, particularly, to a mechanism and technique for applying a patch externally over the vessel puncture.

BACKGROUND

Various cardiovascular procedures, such as angioplasty and stent placement among others, are performed by inserting into and manipulating within the vasculature, wires and catheters adapted to perform those procedures. In coronary vessel procedures access to the vasculature typically is through the femoral artery and is percutaneous, involving insertion of a needle and introducer sheath in the region of the groin to form a track through subcutaneous and extravascular tissue and to puncture and create an arteriotomy in the femoral artery. A short guidewire then is advanced through the needle and into the femoral artery. The needle then is removed and a dilator carrying an introducer sheath then is advanced over the guidewire, the track and into the femoral artery. The dilator enlarges the track and widens the puncture in the vessel. With the distal end of the introducer sheath having been advanced into the vessel, the dilator and guidewire are removed leaving the sheath in place. The sheath provides access into the femoral artery, through the arteriotomy, for catheters and other instrumentalities in order to perform the selected procedure.

After the procedure has been completed, the procedural devices are removed and the arteriotomy must be closed. A number of techniques are known to facilitate closure and healing of the arteriotomy. These include application of pressure at the puncture site for a relatively extended length of time, or the use of biological adhesives or plugs adapted to seal the arteriotomy, or the use of staples or clips. Some closure systems include an arrangement to engage the artery to temporarily draw the edges of the arteriotomy together while a final closure device, such as a stapler, sutures, adhesives or other means is used to effect the permanent closure of the arteriotomy. Some of these system result in piercing the vessel wall or other tissue, such as systems described, for example, in U.S. Pat. No. 6,767,356 (Kanner) and U.S. Pat. No. 6,391,048 (Ginn et al.).

It would be desirable to provide an alternate closure system in which the arteriotomy could be patched entirely outside of the vessel without risking the trauma that may result from piercing the tissue and also to avoid any possibility of a closure element projecting into the interior of the lumen of the vessel. The present invention is directed to such an alternate mechanism and technique to cause hemostasis at the arteriotomy.

SUMMARY OF THE INVENTION

The invention employs a percutaneously placeable device for deploying a patch over the outside of the vessel for closing a puncture therein. The device is advanceable over an indwelling guidewire after the procedural catheters and devices have been withdrawn from the patient. The device includes an elongate shaft associated with an operating mechanism at its proximal end, e.g., a handle. The distal end of the shaft carries a patch in a folded, contracted configuration, the patch being deployable at the site of the vessel puncture in an expanded, sheet-like configuration adapted to be placed exteriorly of the vessel over and about the puncture.

The distal end of the shaft includes an ejection mechanism for unfolding and advancing the patch distally while also pushing and spreading the extravascular tissue away from the region of the puncture to provide a broadened area about the vessel puncture on which to apply the patch. After the patch has been placed, the delivery device can be removed to enable the spread-apart tissue to reform and to close together over the patch. The patch may include an agent to promote hemostasis and clotting.

DESCRIPTION OF THE DRAWINGS

In the accompanying drawings in which components are shown out of scale and in some cases, exaggerated scale for case of explanation and illustration:

FIG. 1 is a somewhat diagrammatic side view of an embodiment of a device that may be used to practice the invention;

FIG. 2 is an enlarged sectional illustration of the distal end of the device as seen along the line 2-2 of FIG. 1;

FIG. 7 is an isometric illustration of the device with the ejection shaft advanced through the outer tube and with the patch disposed about the dilator;

FIG. 8 is an isometric illustration of the distal end of the device loaded with a folded patch in readiness to be inserted into a patient;

DESCRIPTION OF THE ILLUSTRATIVE EMBODIMENTS

Figure 3:
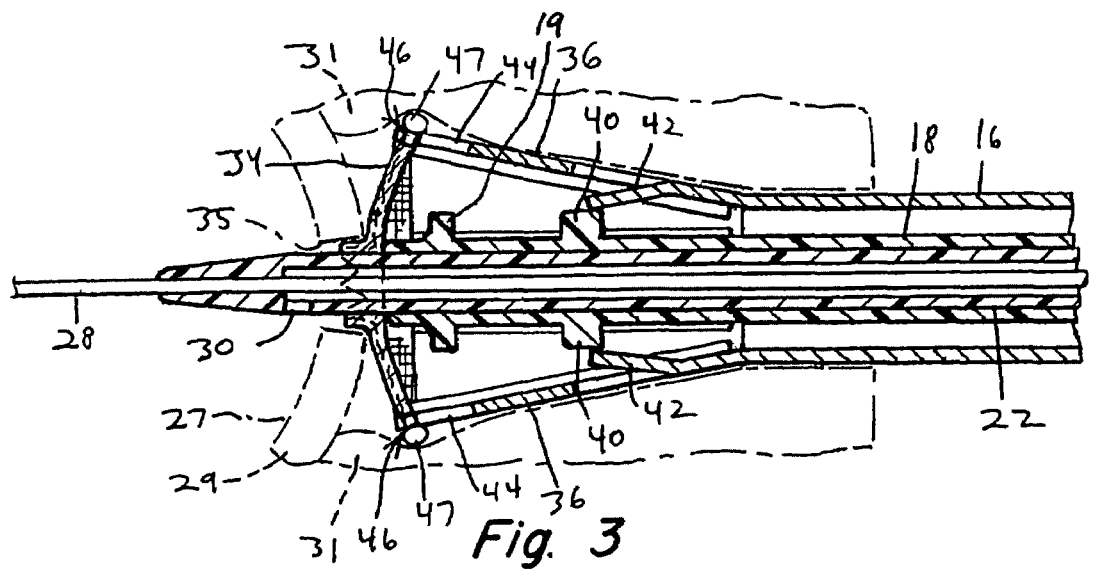
FIG. 3 is a sectional illustration of the device showing, diagrammatically, the manner in which the patch has been advanced distally and unfolded with the tissue about the vessel puncture being pushed aside to facilitate placement of the patch exteriorly of the vessel puncture.
Figure 4:
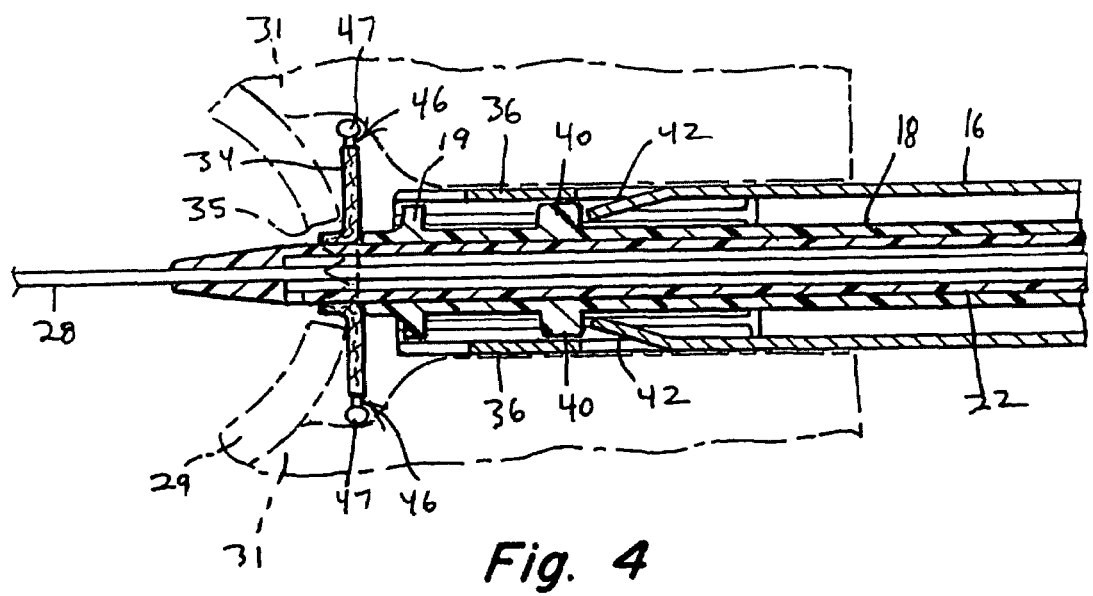
FIG. 4 is a diagrammatic illustration similar to FIG. 3 with the patch having been ejected from the delivery device and in readiness for removal of the delivery device.
Figure 5:
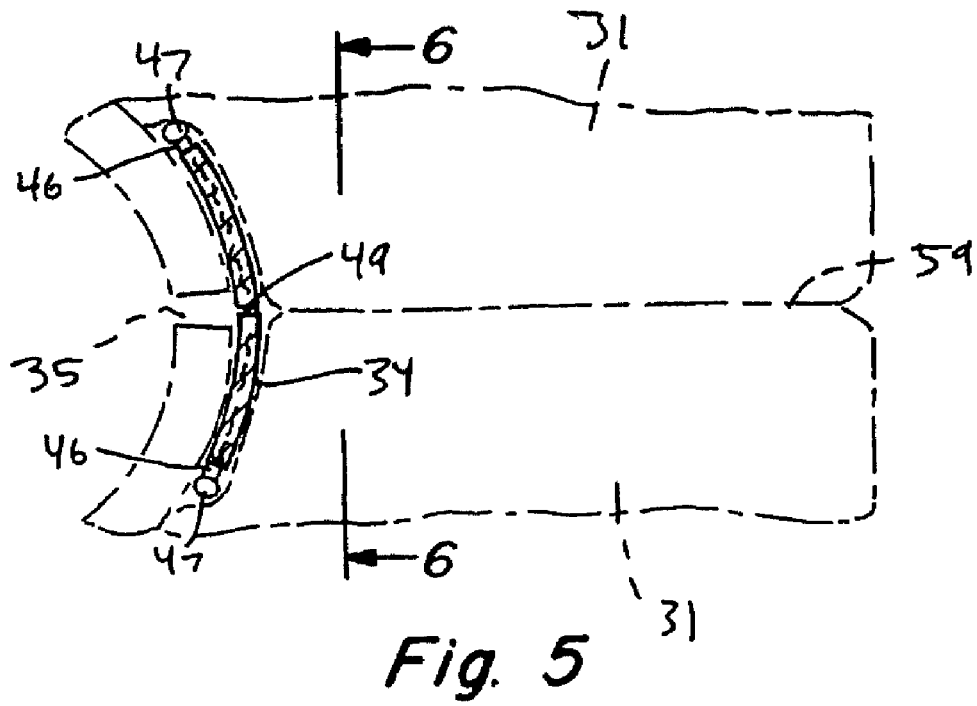
FIG. 5 is a diagrammatic illustration of the vessel and surrounding tissue after the delivery device and indwelling guidewire have been removed, showing the manner in which the tissue has closed about the arteriotomy.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

FIG. 1 illustrates, diagrammatically, a device incorporating the invention including an elongate shaft 10 and a handle 12 or the like at the proximal end for controlling operation of the device to eject and deploy a vascular puncture patch from the distal end 14 of the shaft. As seen more clearly in FIG. 2, the shaft 10 includes an outer tube 16 attached, at its proximal end, to the handle 12. An inner elongate tubular actuator 18 is disposed within the outer tube 16 and is movable longitudinally within the outer tube 16. The handle 12 may include a mechanism 20, such as a slide on the handle 12, to move the actuator tube 18 distally, the slide being connected to the proximal end of the actuator 18. A dilator 22, slidably disposed within the lumen of the actuator 18, has a tapered distal end 24 and a lumen 26 extending the length of dilator 22. Disposed near the distal end of the dilator 22 is a blood marking port 30 that communicates with the dilator lumen 26 to provide the clinician with an indication of when then distal end of the guidewire has been advanced into the lumen 27 of the blood vessel 29. When blood marking port 30 enters the lumen of the blood vessel, blood will flow through the port 30 into the dilator lumen 26 and will exit out of the proximal end 32 of the dilator. It should be understood that the drawings are out of scale with some parts exaggerated in relative size for ease of explanation and clarity. For example, the dilator 22 may be of the order of 5 to 8 French outer diameter (0.065 to 0.104 inch). The actuator tube is slightly larger in diameter, of the order of 8 to 10 French, leaving sufficient clearance between the respective tubes to enable them to move freely relative to each other. The outer tube 16 of the shaft 10 may be of the order of 9 to 13 French outer diameter (0.117 to 0.169 inch).

The distal end of the device is arranged to contain a foldable, expandable puncture patch 34 that, when deployed and ejected from the distal end 14 of the device, is expanded to its unfolded, sheet-like configuration adapted to overlie the exterior of the blood vessel, covering the vessel puncture 35. The folded patch 34 is urged distally toward and out of the distal end of the outer tube 16 by distal advancement of the actuator tube 18 with respect to outer tube 16. The distal end of the actuator tube 18 should be dimensioned to engage the patch and progressively urge it distally until the patch is deployed. A pusher ring 19 may be disposed around the distal end of the actuator tube 18 for pushing against the folds of patch 34 (FIGS. 2 and 12) or for pushing against the central region of patch 34 in the event that the distal tip of actuator tube 18 slips through slits 49 of patch 34, which are described in detail below.

Figure 9:
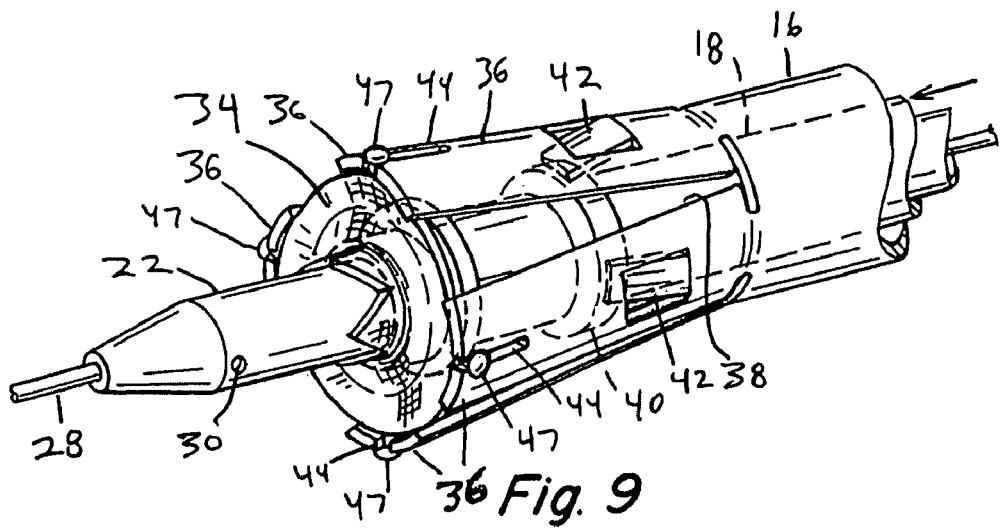
FIG. 9 is an isometric illustration corresponding to FIG. 3.
Figure 10:
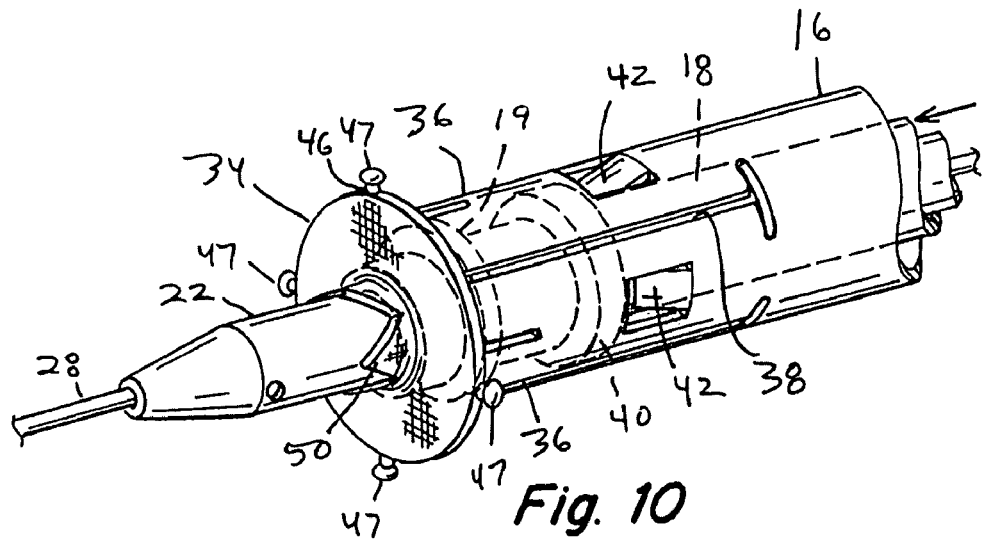
FIG. 10 is an isometric illustration corresponding to FIG. 4.
Figure 11:
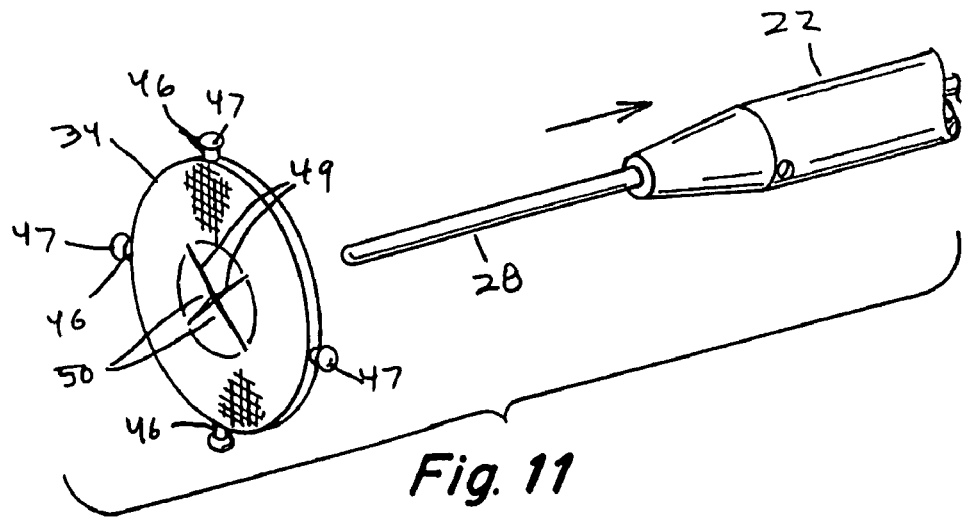
FIG. 11 is an exploded view of an expanded patch, the indwelling guidewire and the distal tip of the dilator.

The distal end of the outer tube 16 is configured to define a plurality of distally extending fingers 36 that can be spread resiliently radially outwardly to a splayed configuration as suggested in FIGS. 3 and 9. As is best seen in FIGS. 9 and 10, the fingers 36 may be defined by a series of longitudinally extending slots 38 formed in the distal end of the outer tube 16 with the proximal ends of the fingers attached to the outer tube in hinge-like fashion. The fingers 36 are caused to be splayed radially outwardly in response to advancement of the actuator 18 concurrently as the actuator advances the patch 34 distally. To that end, and as shown in FIG. 2, the actuator 18 may have one or more radially extending cams 40 having camming surfaces engageable with a plurality of tabs 42 of the fingers 36 that project radially inwardly and distally from each finger 36 within the outer tube 16. The cam 40 may comprise a circumferential ring or ridge around actuator 18, as illustrated in FIG. 7. Alternatively, a plurality of individual cams 40' (FIG. 15) may protrude from the outer surface of actuator 18, each cam 40 being alignable with a corresponding tab 42. As the actuator 18 is advanced distally, the cams 40 engage the tabs 42 to urge the fingers 36 apart (FIGS. 3 and 9). The radially outward splaying of the fingers 36 also serves to push the extravascular tissue about the puncture apart while also causing the patch 34 to unfold to a radially enlarged sheet configuration as the patch 34 is advanced toward ejection from the distal end of the device. The fingers 36 may be formed as an integral part of the outer tube 16, in which case the material from which the outer tube 16 is formed should have sufficient resilience and flexibility to enable the fingers 36 to be splayed outwardly and then, after disengagement of the cams 40 and tabs 42 permit the fingers to return to their relaxed, tubular configuration. Although the illustrative embodiment is shown, somewhat diagrammatically, as having tabs 42 that may be stamped out of the wall of the outer tube 16, it should be understood that the fingers and tabs 42 may take other forms and should have sufficient rigidity to push aside the tissue about the arteriotomy.

Figure 6:
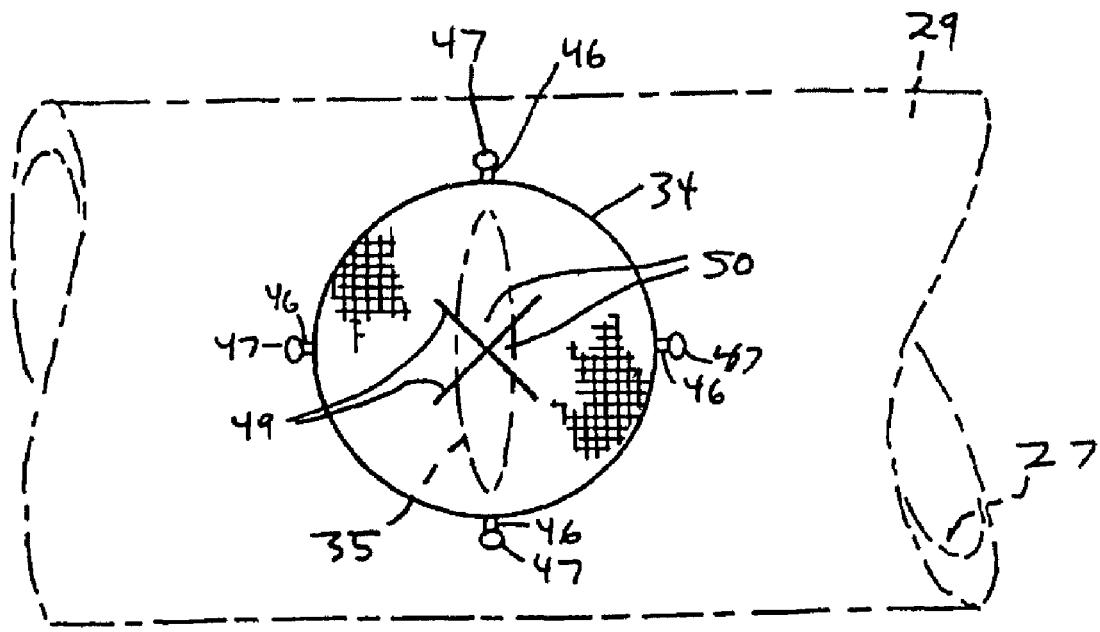
FIG. 6 is a diagrammatic plan illustration of the manner in which the patch overlies the vessel puncture.

Concurrent expansion and distal advancement of the patch 34 may be effected by coupling marginal portions of the patch to the fingers 36 in a manner that allows the patch to advance distally while the progressively spreading fingers 36 expand the patch from its folded to its unfolded configuration (FIG. 9). In the above-described embodiment, the fingers may be provided with guide slots 44 and the patch 34 may be formed to include guidable projections 46 that are received slidably in the guide slots 44. The projections 46 may be formed, for example, by molding the projections 46 onto or as part of the patch from any of a variety of suitable bioabsorbable polymers as are known to those skilled in the art. The projections should be configured to extend through the guide slots 44 with sufficient clearance to enable them to slide freely along and out of the distal ends of their respective slots 44. The ends of the projections may be formed to include enlargements 47 to prevent the projections from withdrawing prematurely from the slots. It should be understood that other configurations may be employed to form projections that are slidably guided within and releasable from the guide slots 44. The patch 34 is provided with cross slits 49 in the center to enable the dilator 22 to pass through the patch. After the patch has been deployed and the dilator removed, the flaps 50 defined by the slits 49 are closed over the vessel puncture (FIG. 6). The patch may be formed from a variety of suitable biocompatible materials including, for example, fabrics formed from chitosan or other biocompatible materials capable of being folded and unfolded in accordance with the invention. The material may be bioabsorbable, its function having been served after hemostasis has been accomplished.

The parts of the device are configured so that when the patch 34 has been advanced beyond the distal end of the outer tube 16 and has spread to its unfolded configuration, the fingers 36 of the outer tube 16 return, resiliently, to their original unsplayed configuration. To that end, the lengths of the tabs 42 and the location of the cam 40 along the actuator 18 are such that the cam 40 will advance past the ends of the tabs 42 at or just after the time that the patch 34 is released from its engagement with the fingers 36. The resilience of the distal fingers 36 is such that they will return radially inward to their original, unsplayed configuration. When the fingers have returned to their original position, the distal ends of the fingers are in a position to be urged against the patch to assure firm contact of the patch with the extravascular surface about the vessel puncture.

The device is used after the vascular procedural devices, such as catheters, stents and stent delivery devices, etc., have been removed from the patient, leaving only the guidewire 28 in place. The vascular closure device then can be back loaded onto the proximal end of the guidewire by inserting the proximal end of the guidewire into the lumen at the distal end 24 of the dilator 22. Then the dilator and other components of the patch delivery device are advanced over the guidewire, with the dilator being advanced through the vessel puncture into the blood vessel. The presence of blood at the proximal end 32 of the dilator 22 indicates that the blood marking port 30 has advanced into the vessel. The outer tube 16 and the dilator 22 are disposed relative to each other so that when blood just begins to appear at the proximal end of the blood marking lumen, the distal end of the outer tube will be located just outside and in proximity to the vessel puncture. The relative positions of the dilator 22 and outer tube 16 may be fixed by providing abutting surfaces or stops on the tube 16 and dilator or on the portions of the handle that control relative movement between the two components to limit the extent that the distal end 24 of the dilator projects beyond the distal end of the tube 16. By providing a fixed distance between the blood marking port 30 on the dilator 22 and the distal end of the outer tube 16, the clinician can verify the location of the distal end of the device with respect to the vessel puncture.

When the distal end of the delivery catheter has been advanced into a position in proximity to the vessel puncture, the actuator 18 may be advanced distally, as by operation of the slide 20, to cause the patch 34 to be spread while advancing it distally and ejecting it from the catheter and while also pushing aside adjacent tissue externally of the vessel. When the fingers 36 have returned to their relaxed position, the catheter may be urged lightly in a distal direction to lightly press the patch against the region about the puncture. With the patch so placed, the delivery device may be removed, together with the guidewire. The natural tendency for the displaced tissue and tissue through which the original catheter track 59 was formed is to come together to close over the patch. This may be enhanced by external pressure applied to the patient. It may be noted that with this mode of hemostasis the edges of the vessel puncture may not be completely closed together and that some blood leakage may be expected. However, where the surrounding tissue and patch overlie the puncture, it is anticipated that blood will form sufficient clot to have a hemostatic effect enabling and containing clotting at the puncture site. It may be noted that although the patch will have one or more slits in its center in order to accommodate the dilator, the slits will close together under the influence of the pressure of the surrounding tissue and externally applied pressure.

Figure 12:
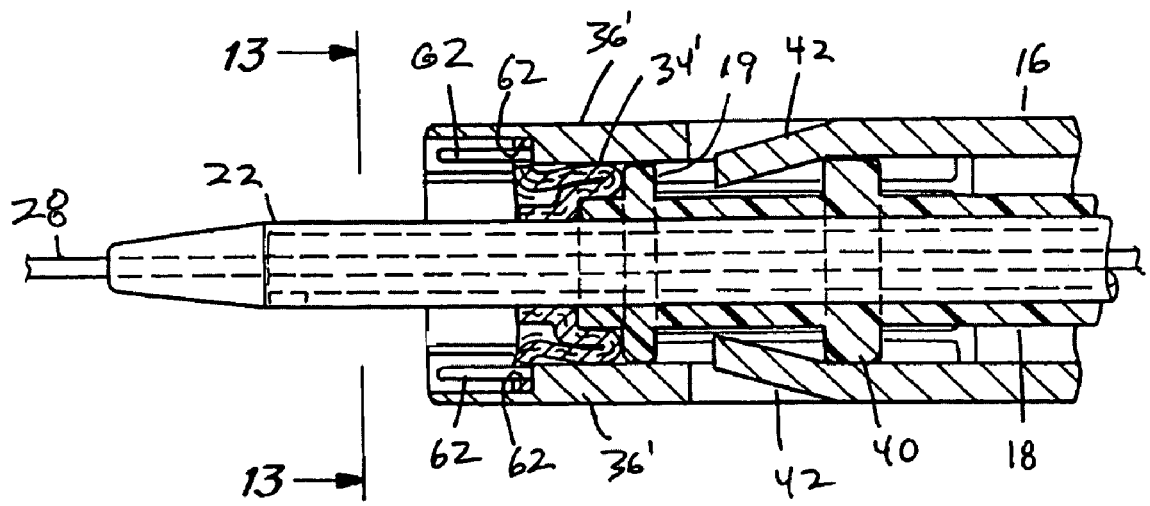
FIG. 12 is somewhat diagrammatic longitudinal cross-section of another embodiment of the invention.
Figure 13:
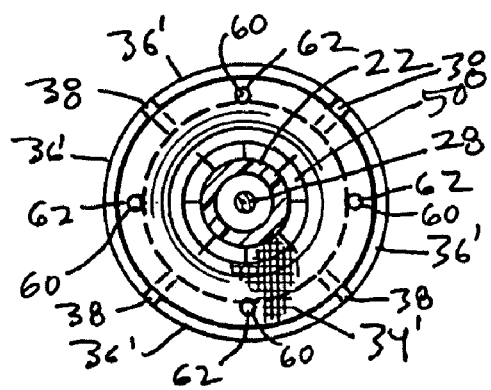
FIG. 13 is an end view of FIG. 12 as seen along the line 13-13 of FIG. 12.
Figure 14:
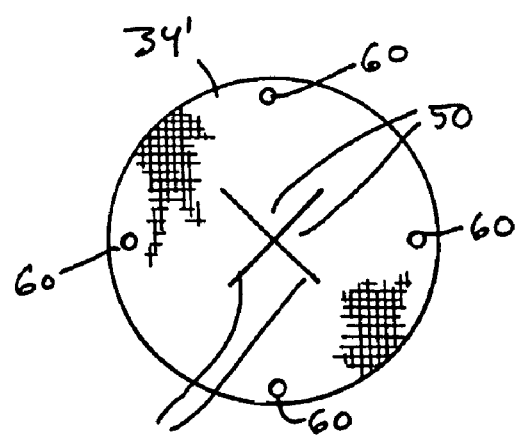
FIG. 14 is a plan view of a patch for use with an embodiment as that of FIGS. 12 and 13.

FIGS. 12 and 13 illustrate another embodiment of the invention having a modified form of connection between the patch 34' and expandable fingers 36' at the distal end of the deployment device. In this embodiment, the patch 34' (FIG. 14) is provided with a plurality of apertures 60 arranged about and adjacent to the perimeter of the patch and the delivery device includes a plurality of distally extending pins 62 mounted to the fingers 36'. The patch 34' is mounted on the pins 62 which extend through the apertures 60. When the actuator 18 is advanced to spread the fingers 36' and also advance the patch 34', the patch may slide along the pins 62 until it separates from the guide pins 62 and fingers 36'. Once the patch has been released, the device functions and is operated in the same manner as described above.

Figure 15:
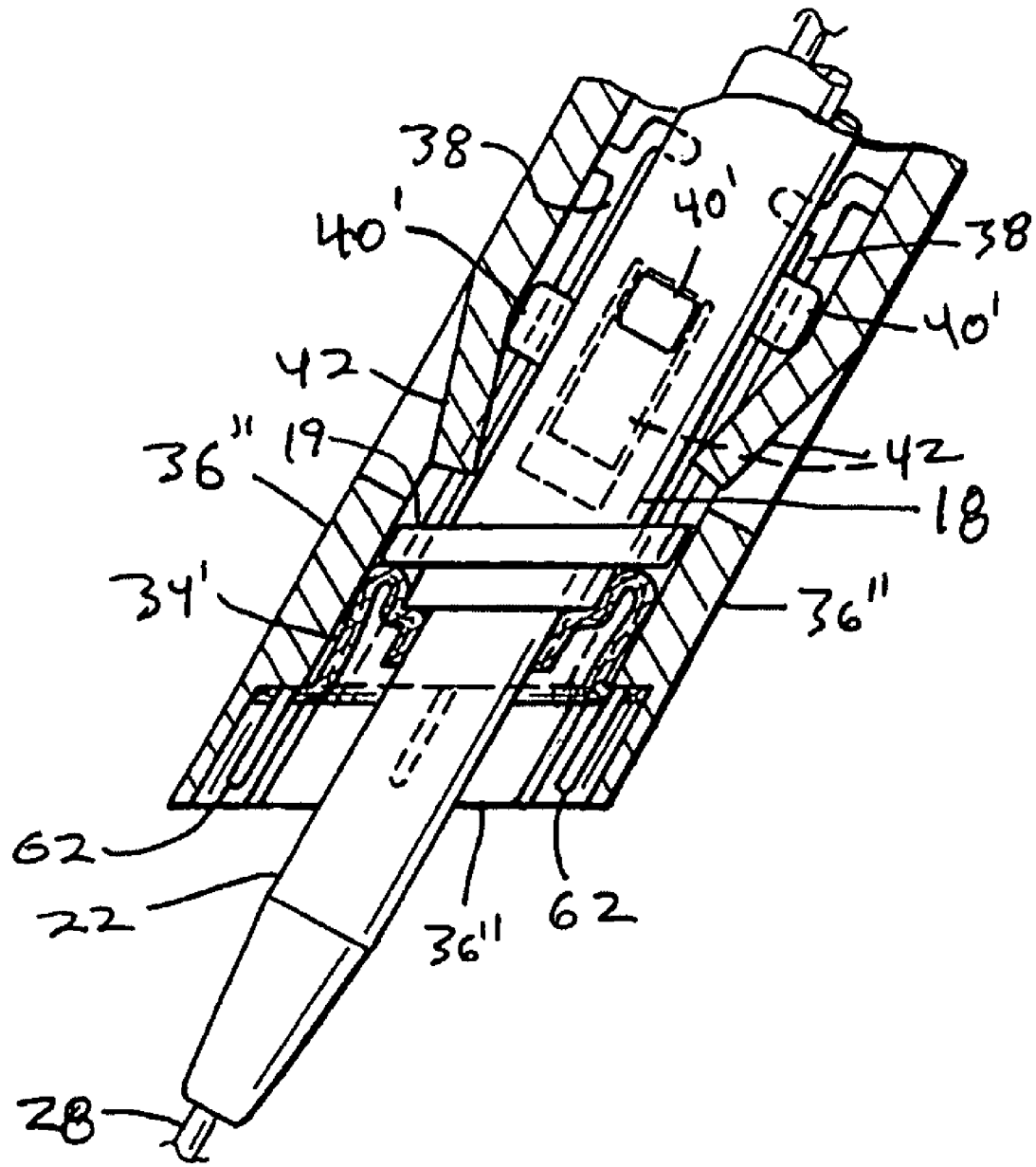
FIG. 15 is an illustration of the distal end of a modified form of the device in which the distal end is formed to be oblique to the longitudinal axis.

FIG. 15 illustrates a modified form of the device that may be used more conveniently when the approach angle of the needle and catheters is other than orthogonal to the vessel, for example, of the order of about 45°. In this embodiment the distal end of the outer tube 16 should be formed at an oblique angle in which one or more of the fingers 36" will be longer than the others. In this embodiment, the patch 34" will be oriented within the outer tube at an angle, as shown. Similarly, the distal end of the actuator may be formed at the oblique angle. The cams 40' should be located with respect to the tabs 42 to engage them simultaneously to cause the fingers to splay and then contract as described above. By forming these elements with the oblique angle generally corresponding to the approach angle of the devices, the patch may be laid directly over and urged against the puncture in the vessel even when the approach angle is other than orthogonal.

It should be understood that the foregoing description of the invention is intended merely to be illustrative thereof and that other embodiments, modifications and equivalents may be apparent to those skilled in the art while remaining within the scope of the invention.

We claim:

1. An apparatus for percutaneously effecting hemostasis at a vascular puncture comprising:
   a shaft having proximal and distal ends, the shaft including an outer tube having a distal end with a plurality of resiliently hinged fingers adapted to be urged from a tubular configuration to a splayed configuration;
   a flexible folded biocompatible puncture patch disposed in the distal end of the outer tube;
   the fingers having guide slots and the patch having guidable projections slidably received in the guide slots to enable the fingers to unfold the patch while the fingers are urged radially outward to a splayed configuration, the guide slots enabling concurrent distal movement of the patch and its guidable projections relative to the fingers to enable the patch to be ejected from the distal end of the device in an unfolded configuration;
   an actuator movable distally within the outer tube to engage the patch within the outer tube to advance the patch distally; and
   each of the fingers having an inwardly projecting tab engageable by the actuator to urge the fingers progressively radially outwardly in response to progressive distal advancement of the actuator;
   whereby advancement of the actuator causes unfolding of the patch and ejection of the patch from the distal end of the device.

2. The apparatus as defined in claim 1 wherein the inwardly projecting tabs of the fingers and the actuator are configured to disengage when the patch has been ejected to enable the fingers to return resiliently to their unsplayed tubular configuration thereby enabling the distal ends of the fingers to be engaged with the deployed patch to urge the patch against the region of the vascular puncture.

3. The apparatus as defined in claim 1 wherein the shaft has a longitudinal axis and wherein the distal ends of the outer tube and the actuator extend along an angle oblique to the axis.

4. The apparatus as defined in claim 1 further comprising:
   the inwardly projecting tab on each of the fingers being defined by a portion of the finger, the actuator having radially extending camming surfaces engageable with the inwardly projecting tabs of the fingers as the actuator is advanced distally.

5. The apparatus as defined in claim 1 further comprising:
   the actuator having a lumen extending therethrough; and
   a dilator slidably mounted within the lumen of the actuator, the dilator having a tapered distal end and a guidewire lumen extending through the dilator.

6. The apparatus as defined in claim 5 wherein the patch comprises a plurality of radially extending slits formed about the center of the patch, the slits defining flaps adapted to flex to enable the patch to advance over the dilator, the flaps being adapted to close when the patch is released and urged against the region about the vascular puncture.

7. The apparatus as defined in claim 5 further comprising a blood marking aperture in the distal end of the dilator.

* * * * *